United States Patent
Autuori et al.

(10) Patent No.: US 7,157,099 B2
(45) Date of Patent: Jan. 2, 2007

(54) SUSTAINED RELEASE PHARMACEUTICAL COMPOSITIONS FOR THE PARENTERAL ADMINISTRATION OF HYDROPHILIC COMPOUNDS

(75) Inventors: Francesco Autuori, Cinisello Balsamo (IT); Carlo Bianchini, Cinisello Balsamo (IT); Giuseppe Bottoni, Cinisello Balsamo (IT); Flavio Leoni, Cinisello Balsamo (IT); Paolo Mascagni, Cinisello Balsamo (IT); Valmen Monzani, Cinisello Balsamo (IT); Oreste Piccolo, Cinisello Balsamo (IT)

(73) Assignee: Italfarmaco S.p.A., Milan (IT)

( * ) Notice: Subject to any disclaimer, the term of this patent is extended or adjusted under 35 U.S.C. 154(b) by 619 days.

(21) Appl. No.: 10/258,616

(22) PCT Filed: May 23, 2001

(86) PCT No.: PCT/EP01/05949

§ 371 (c)(1),
(2), (4) Date: Nov. 6, 2002

(87) PCT Pub. No.: WO01/89479

PCT Pub. Date: Nov. 29, 2001

(65) Prior Publication Data

US 2003/0171299 A1    Sep. 11, 2003

(30) Foreign Application Priority Data

May 26, 2000    (IT) .......................... MI2000A1173

(51) Int. Cl.
*A61K 9/127*    (2006.01)

(52) U.S. Cl. ..................................................... 424/450
(58) Field of Classification Search ................. 424/450
See application file for complete search history.

(56) References Cited

U.S. PATENT DOCUMENTS 6,861,064 B1 *   3/2005   Laakso et al. ............... 424/408

FOREIGN PATENT DOCUMENTS

| WO | 94 08610 | 4/1994 |
|----|----------|--------|
| WO | 99 21533 | 5/1999 |

OTHER PUBLICATIONS

M.R. Gasco et al.: "Long-acting delivery systems for peptides reduced plasma testosterone levels in male rats after a single injection" International Journal of Pharmaceutics (Amsterdam), vol. 62, No. 2-3, pp. 119-124 1990.

M. Bello et al.: "Pertechnetate release from a water/oil microemulsion and an aqueous solution after subcutaneous injection in rabbits" Journal of Pharmacy and Pharmacology, vol. 46, No. 6, pp. 508-510.

S. Bjerregaard et al.: "Sustained elevated plasma aprotinin concentration in mice following intraperitoneal injections of w/o emulsions incorporating aprotinin" Journal of Controlled Release, vol. 71, No. 1, pp. 87-98 Mar. 12, 2001.

* cited by examiner

*Primary Examiner*—Carlos A. Azpuru
(74) *Attorney, Agent, or Firm*—Oblon, Spivak, McClelland, Maier & Neustadt, P.C.

(57) ABSTRACT

Stable, biologically compatible pharmaceutical compositions in the form of water-in-oil microemulsions (w/o), for the sustained release by parenteral administration of active ingredients which are hydrophilic or are made hydrophilic by suitable derivatization, a process for the preparation of said microemulsions and the use thereof.

22 Claims, 2 Drawing Sheets

Figure 1:
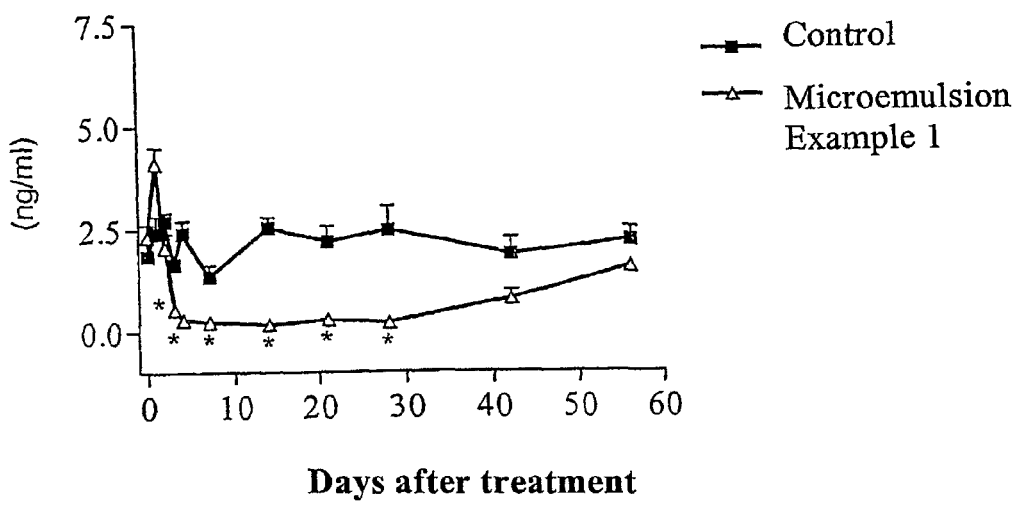
Figure 1:
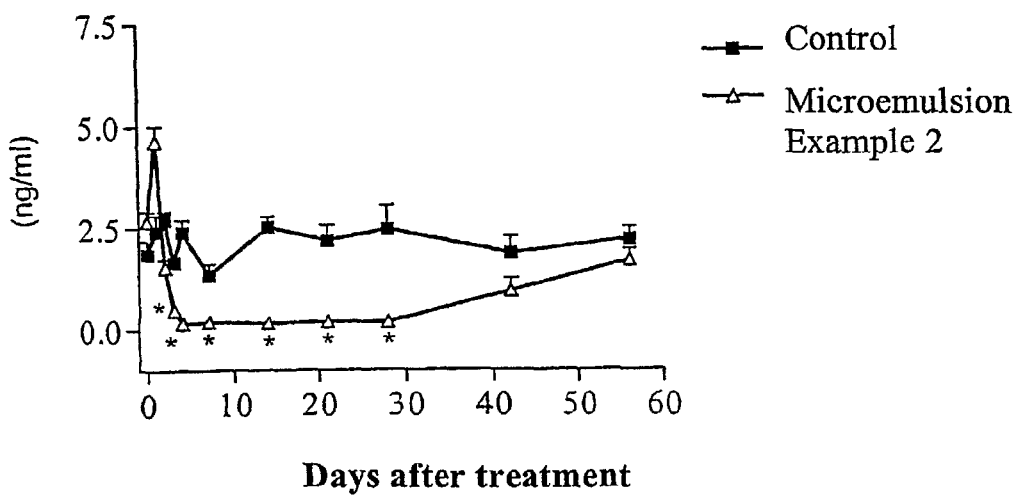

Effect of the microemulsions of Examples 1 and 2 on testosterone serum levels in rats.

\* p<0.001 vs. Control (ANOVA test and Bonferroni t test for multiple comparisons)

\* p<0.001 vs. Control (ANOVA test and Bonferroni t test for multiple comparisons)

SUSTAINED RELEASE PHARMACEUTICAL COMPOSITIONS FOR THE PARENTERAL ADMINISTRATION OF HYDROPHILIC COMPOUNDS

FIELD OF THE INVENTION

The present invention relates to sustained release pharmaceutical compositions for the parenteral administration of active ingredients which are hydrophilic or are made hydrophilic by suitable derivatization, in the form of stable, biologically compatible and easily preparable water-in-oil microemulsions (w/o). More particularly, peptide active ingredients or biologically active oligo- or polysaccharides, for which protection from the immediate attack by the hydrolytic enzymes present in living organisms as well as sustained release in time, to avoid repeated administrations, are desirable, are advantageously formulated through said microemulsions. Said formulations for the therapeutical use can be injected without problems or significant side effects and are easily prepared industrially, providing a remarkable technical improvement.

PRIOR ART

Microemulsions can be generally defined as optically isotropic systems, not birifrangent under polarized light observation, transparent, thermodynamically stable, of extremely reduced size, with droplet diameter ranging from 5 to 200 nm, produced by dispersion of two immiscible liquids which are stabilized by the presence of emulsifiers, which modify the chemical-physical properties of the separation surface between the two liquids, reducing substantially to zero the interfacial tension. An oil, water, a surfactant or tenside and optionally of a co-surfactant o co-tenside should usually be present for microemulsions to form; the tendency to form a water-in-oil (w/o) or oil-in-water (o/w) microemulsion depends on the mutual proportions of aqueous and oily phases as well as on the nature of the surfactant. In particular, ternary phase diagrams having as components water, a hydrophobic compound and a mixture of surfactant and co-surfactant, obtained according to experimental data, allow to single out the area in which w/o and o/w microemulsions exist and are stable. For example, Aboofazeli et al (Int.J.Pharm. 111 (1994) 63–72) studied the capability of various compounds having co-surfactant action to form w/o microemulsions. The system studied by the Authors consisted of mixtures of a fatty acid ester, a 1:1 lecithin-co-surfactant and water in various ratios. An efficiency scale of the compounds used as co-surfactants has been defined: primary amines>alcohols>fatty acids. Furthermore, the efficiency proved to be related with the length of the alkyl chain of the alcohol and of the respective fatty acid; hence butanol>pentanol>hexanol>pentanoic acid>hexanoic acid. On the basis of these experimental data, alcohols such as butanol and pentanol and, to a less extent, the corresponding fatty acids, appear to be the best candidates. The use of the described compounds allows to prepare stable w/o microemulsions, but does not ensure the tolerability of said formulations, particularly for the depot use wherein the formulation and the subcutaneous or intramuscular tissue remain in contact for days or even weeks.

Moreover, literature reports that the co-surfactant to surfactant ratio is critical; the data reported by Aboofazeli et al. relate to a 1:1 ratio between the two components. Atwood et al (Int.J.Pharmacy 84 R5 (1992)) studied the behaviour of lecithin/water/fatty acid ester/butanol mixtures wherein the surfactant/co-surfactant ratio is increased from about 1.7 to 3. The Authors evidenced that the decrease of the co-surfactant amount in favor of lecithin dramatically restricts the area in which the presence of a w/o microemulsion is observed, even when using a remarkably efficient co-surfactant such as butanol.

Surfactants are generally classified according to an empirical scale, known as hydrophile-lipophile balance (HLB) which assignes values ranging from 1 to 40. As a rule, suitable surfactants for w/o microemulsions have low HLB whereas those suitable for o/w microemulsions have high HLB. When the interfacial tension is $<2 \times 10^{-2}$ dyn/cm, a stable microemulsion can form. The optional presence of a co-surfactant allows to increase the interfacial fluidity, as the co-surfactant molecules penetrate between the surfactant molecules, thereby producing a dishomogeneous surface film. Co-surfactants can also decrease the aqueous phase hydrophilia and hence the interfacial tension between the two phases. In principle, the use of co-surfactants is advantageous in that they allow to decrease the amount of necessary surfactant while increasing the stability of the microemulsion; however, as already mentioned above, it is preferable to limit their use as they have potential topical toxicity, mainly in case of contact between the carrier and the subcutaneous or intramuscular tissues for prolonged times.

The numerous advantages of the use of a microemulsion as a carrier for active ingredients are known.

Microemulsions, under specific conditions of ratios between the components, can form spontaneously without need for high power for the preparation thereof; therefore their preparation on an industrial scale can be easy. Said spontaneous microemulsions are thermodynamically stable, homogeneous and transparent, so that they can be monitored by spectroscopical techniques. Microemulsions with mean diameters <100 nm can be prepared, which can be cold sterilized by filtration trough 0.22 micron membrane commercial filters. The microemulsions can allow to administer poorly soluble or poorly stable drugs.

Furthermore said systems can undergo phase inversion when an excess of the dispersed phase is present, or as a consequence of a change of temperature: this property can affect the bioavailability of the active ingredient with a mechanism that has not yet been clarified.

The w/o microemulsions can control the release of the active ingredient or protract its stability in physiologic fluids through protection from the action of hydrolytic enzymes. A number of reviews on microemulsions exist, for example "Industrial application of microemulsions" Marcel Dekker Ed. 1997, which in the chapter "Microemulsions in the Pharmaceutical field: perspectives and applications" deals with the usefulness thereof in the pharmaceutical field, and "Handbook of Microemulsion Technology", Ed. Kumar Mittal (1999) concerning the chemical-physical aspects.

The use of w/o microemulsions as vehicles to obtain a controlled release of active ingredients which are hydrophilic or are made hydrophilic by suitable derivatization, is reported in the patent literature.

In particular, as for biodegradable molecules such as peptides, the parenteral administration of w/o microemulsions containing said active ingredients is reported in a study [M. R. Gasco et al., Int.J.Pharm., 62, 119 (1990)] wherein an LHRH hormone analog, formulated in a microemulsion consisting of components considered biocompatible and containing 500 µg/ml of the active ingredient, administered by single intramuscular injection at doses of 3 mg/Kg in adult male rats weighing about 200 g, decreased testosterone plasma levels for a time up to about 30 days after the injection; said levels were lower than those observed in a second group of mice treated with repeated injections (one a day for 28 days) at doses of 100 μg/Kg of active ingredient in buffer solution.

It should however be noted that the decrease in the testosterone concentration was not homogeneous in time during observation, and it became therapeutically effective only 8 days after the administration.

This delay in the therapeutical effect is not very advantageous, particularly in the treatment of prostate tumor which is known to require testosterone for growing; therefore the faster the testosterone normal production is stopped, the more effective the treatment.

The above mentioned paper shows the effectiveness of a w/o microemulsion consisting of ethyl oleate (60.5%), water (10.1%), phosphatidyl choline (18.9%) and caproic acid (10.5%) for the sustained release of the peptide. The surfactant (phosphatidylcholine) to co-surfactant (caproic acid) ratio is 1.8. The components of said microemulsion, individually taken, are considered biologically compatible by the Authors. No mention is made of the biocompatibility of the microemulsion as a whole neither of the condition of the subcutaneous tissue in contact with the formulation.

According to the teaching of said paper, a w/o microemulsion containing Leuprolide acetate as active ingredient with LHRH activity was prepared, consisting of ethyl oleate (66.9%), water (9.7%), phosphatidyl choline (19.4%) and a caproic acid/butyric acid 3/1 mixture (3.9%). According to this paper, the mixture with butyric acid was used instead of caproic acid alone in order to minimize the surfactant to co-surfactant ratio, which is in this case 4.9 instead of 1.8. The in vivo test carried out by subcutaneous injection of the product in the rat has confirmed the effectiveness but has also surprisingly shown alarming local ulcerogenicity and persistent formation of subcutaneous granulomas. This pharmacologically unacceptable result, notwithstanding the lower amounts of co-surfactants used, proved that the biocompatibility of the single components of the microemulsion was not sufficient to ensure the biocompatibility of the mixture constituting the microemulsion, when used for the parenteral administration.

Similarly, the mixtures disclosed and claimed in various patents, e.g. WO 94/08610, although providing stable microemulsions and possible controlled releases of the active ingredient in time, do not teach to those skilled in the art how to obtain the sustained release of an hydrophilic active ingredient while avoiding such side effects. Said microemulsions usually consist, in fact, of water, an oily component, a surfactant, a co-surfactant, and optionally electrolytes, in various ratios. Neither biocompatibility of the microemulsion "in toto" is evaluated, nor the necessary ratios of mixture components to active ingredient are indicated, to obtain stability of both the active ingredient and the microemulsion as well as biocompatibility of the formulation.

On the other hand, said patents did not specifically consider the problems concerning local tolerability connected with intramuscular (i.m.) and subcutaneous (s.c.) administrations, which are the most suitable and easy routes for the parenteral administration.

An alternative technology already used at the industrial level for the sustained release of peptides is that described and claimed in a number of patents, inter alia U.S. Pat. No. 3,976,071, wherein such release is obtained by the use of bioerodible polymers in which the active ingredient is inbodyrated. Typical examples of bioerodible polymers are polymers based on glycolic acid and lactic acid. The drawback of said technology is that it is relatively expensive and troublesome compared with the above described microemulsions, furthermore it requires the use of organic, in particular chlorinated, solvents during the preparation, which involves problems in terms of environmental impact and safety of the pharmaceutical formulation.

On the other hand, said formulations advantageously cause not persistent granulomas and do not induce local ulcerogenicity.

DISCLOSURE OF THE INVENTION

The present invention aims at providing sustained release pharmaceutical compositions in the form of stable w/o microemulsions, which are easy to prepare, can be sterilized, are free from remarkable systemic or topical side effects, are suitable for parenterally administering, preferably i.m. or s.c., active ingredients which are hydrophilic or are made hydrophilic through suitable derivatization, thereby obtaining a remarkable technical improvement compared with the known technique.

A procedure has been found, consisting in the clinical, post-mortem, and histological examinations of the animals treated with the above mentioned microemulsions, suitable for thoroughly evaluating the biocompatibility of any formulations for the sustained release administration.

According to this procedure, a microemulsion is considered acceptable, according to what stated in literature (Protein Formulation and Delivery—F. J. McKelly 2000 pages 245–247), when any local swelling, more or less marked depending on the administered dose, is anyway reversible; on the other hand, a similar tissular response is also observed for materials considered biodegradable, which response is apparently important in affecting the sustained release of the drug in time. A local intolerance in the form of persistent ulcerations is conversely considered unacceptable.

The microemulsions of the present invention consists for up to 20% of an internal hydrophilic aqueous phase containing the active ingredient, for 30 to 98% of a hydrophobic external phase and for up to 50% of a surfactant alone or in admixture with a co-surfactant. The microemulsion preferably contains a percentage $\leq 35\%$ of surfactant and co-surfactant, with a surfactant/co-surfactant ratio $\geq 2$, and most preferably $\geq 3,5$.

Other biologically compatible excipients which do not affect the stability of the microemulsion can also be present.

Suitable surfactants for the microemulsions of the invention are selected from natural or synthetic glycerophospholipids containing residues of $C_4$–$C_{20}$ saturated or unsaturated carboxylic acids, having as phosphoester moiety a residue of choline, ethanolamine, serine, glycerol; cholesterol; $C_{12}$–$C_{20}$ fatty acid esters of sugars such as sorbitol, galactose, glucose, saccharose; polyoxyethylene sorbitan $C_{12}$–$C_{20}$ fatty acid esters.

The optionally present co-surfactants are selected from $C_8$–$C_{20}$ fatty acids, $C_2$–$C_{14}$ polyhydroxyalkanes, particularly propylene glycol, hexanediol and glycerol, $C_2$–$C_{12}$ alcohols, esters of lactic acid with a $C_2$–$C_8$ alcohol residue.

The hydrophobic continuous phase is selected from the following compounds, alone or in mixture: esters of $C_8$–$C_{20}$ saturated or unsaturated carboxylic acids with a $C_2$–$C_8$ alcohol residue or mono, di- and triglycerids of $C_8$–$C_{20}$ fatty acids, or vegetable oils suitable for the parenteral administration, such as soybean, peanut, sesame, cottonseed, sunflower oils.

The microemulsions of the invention are further characterized by pH ranging from 4.5 to 7.5, preferably from 5 to 7, said pH, when not intrinsic to the composition of the microemulsion, being preferably obtained by addition of a suitable amount of a natural amino acid to the microemulsion without affecting its stability and the average size of the droplets.

The w/o microemulsions of the invention are particularly suitable as carriers for peptides, in particular LHRH analogs such as Leuprolide acetate, Goserelin, Triptorelin, Nafarelin acetate, Histrelin, Cetrorelix or the corresponding acetates, or peptides such as Somatostatin or its analogs such as Octreotide and Lanreotide acetate.

Furthermore, the microemulsions of the invention are particularly suitable as carriers for polysaccharides, in particular unfractioned heparin or low molecular weight heparins.

The microemulsions of the invention allow to prepare formulations with sustained release of hydrophilic active ingredients. Said sustained release formulations, which are a further object of the invention, induce no local ulcerogenicity and produce non persistent granulomas, which are reabsorbed during the time in which the medicament is effective. In the case of LHRH-type peptides, and in particular Leuprolide, Goserelin, Triptorelin, Nafarelin acetate, Histrelin, Cetrorelix and the corresponding acetates, sustained release for at least 30 days can be obtained. In the case of Somatostatin, Octreotide and Lanreotide, sustained release for at least 8 days can be obtained.

The invention further relates to the use of a microemulsion according to the invention comprising Leuprolide, Goserelin, Triptorelin, Nafarelin acetate, Histrelin, Cetrorelix or the corresponding acetates for the preparation of a medicament for suppressing testosterone production after single administration for at least 30 days, where testosterone level already decreases 48 h after the administration.

The invention also relates to the use of the microemulsions containing Octreotide or its analogues for the preparation of a medicament for suppressing growth hormone production for at least 8 days.

A further object of the present invention is the use of the microemulsions containing unfractioned heparin or low molecular weight heparins for the preparation of sustained release medicaments upon single administration.

The following examples further illustrate the present invention.

EXAMPLE 1

Preparation of a w/o Microemulsion Containing Leuprolide Acetate a) Preparation of the Aqueous Phase 350 mg of Leuprolide acetate are dissolved in 10 ml of water for injections added with 200 mg of lysine.

b) Preparation of the Oily Phase 60 g of ethyl oleate, 25 g of soy lecithin (purity >95%) and 5 g of caprylic acid are mixed separately, in a suitable vessel thermostatized at a temperature of 60–70° C., under stirring. The resulting clear homogeneous solution is cooled at room temperature.

c) Preparation of the Microemulsion

The aqueous phase (solution a) is added to the oily phase (solution b) under stirring, to obtain an optically transparent, homogeneous microemulsion. A pH value of about 6 was evaluated based on the used amounts of lysine and caprylic acid fraction soluble in the aqueous phase.

Said microemulsion is sterile filtered through a suitable 0.22 μm membrane.

The Leuprolide acetate content of said microemulsion was evaluated by HPLC analysis in the following conditions:

| | |
|---|---|
| Stationary phase: | Vydac C18 5 μ column (250 × 4 mm) |
| Mobile phase A: | $H_2O$ + 0.1% TFA |
| B: | $CH_3OH$ + 0.1% TFA |
| Gradient: | 20' 100% A to 100% B |
| Flow: | 0.8 ml/min |
| Detector: | UV 214 nm |

The content in Leuprolide acetate is 3 mg/ml.

EXAMPLE 2

Preparation of a w/o Microemulsion Containing Leuprolide Acetate

The procedure of Example 1 is followed, but solubilizing 600 mg of Leuprolide acetate in 10 ml of water.

EXAMPLE 3

Preparation of a w/o Microemulsion Containing Leuprolide Acetate

The procedure of Example 1 is followed, but without adding 200 mg of lysine. Calculated pH is about 3.

EXAMPLE 4

Preparation of a w/o Microemulsion Containing Leuprolide Acetate

The procedure of Example 1 is followed, but solubilizing 900 mg of Leuprolide acetate in 10 ml of water.

EXAMPLE 5

Preparation of a w/o Microemulsion Containing Leuprolide Acetate

The procedure of Example 1 is followed, but changing the amounts of surfactant and co-surfactant to 15 g of soy lecithin and 3 g of caprylic acid, respectively. In this way, although keeping the ratio between the two components unchanged (5:1) the total amount of the surfactant/co-surfactant mixture is changed from 30% to 18%.

EXAMPLE 6

Preparation of a w/o Microemulsion Containing Octreotide

The procedure of Example 1 is followed, but solubilizing 3 g of Octreotide in 10 ml of water, instead of 350 mg of Leuprolide acetate in 10 ml of water.

EXAMPLE 7

Preparation of a w/o Microemulsion Containing Heparin

The procedure of Example 1 is followed, but solubilizing in 10 ml of water 50 mg of unfractioned heparin in the form of calcium or sodium salt, instead of 350 mg of Leuprolide acetate.

EXAMPLE 8

Preparation of a w/o Microemulsion Containing Leuprolide Acetate

The procedure of Example 1 is followed, but changing the quali-quantitative composition of the oily phase: ethyl oleate (66.9%), phosphatidyl choline (19.4%) and a 3:1 caproic acid-butyric acid mixture (totally 3.9%).

EXAMPLE 9

Preparation of a w/o Microemulsion Containing Leuprolide Acetate a) Preparation of the Aqueous Phase
60 mg of Leuprolide acetate are dissolved in 0.6 ml of water for injections added with 8 mg of lysine.
b) Preparation of the Oily Phase
2.1 g of ethyl oleate, 215 mg of polyoxyethylene sorbitan monooleate and 1 g of soy lecithin are mixed in a suitable vessel, heating at 50° C. under stirring. The resulting clear homogeneous mixture is cooled at room temperature.
The aqueous solution is slowly added in portions to the oily mixture under stirring, to obtain an optically clear microemulsion containing 1.5% of Leuprolide acetate.

EXAMPLE 10

Preparation of a w/o Microemulsion Containing Leuprolide Acetate a) Preparation of the Aqueous Phase
60 mg of Leuprolide acetate are dissolved in 0.2 ml of water for injections added with 4.1 mg of lysine.
b) Preparation of the Oily Phase
1.2 g of ethyl oleate, 0.5 g of polyoxyethylene sorbitan monooleate and 0.1 g of caprylic acid are mixed in a suitable vessel, heating to 50° C. under stirring. The resulting clear homogeneous mixture is cooled at room temperature.
The aqueous solution is slowly added in portions to the oily mixture under stirring, to obtain an optically clear microemulsion containing 3 mg/ml of Leuprolide acetate.

EXAMPLE 11

Preparation of a w/o Microemulsion Containing Octreotide Acetate a) Preparation of the Aqueous Phase
20 mg of Octreotide acetate are dissolved in 0.2 ml of water for injections containing 0.2 g of propylene glycol and 4 mg of lysine.
b) Preparation of the Oily Phase
0.98 g of ethyl oleate, 0.5 g of soy lecithin and 0.1 g of caprylic acid are mixed in a suitable vessel, heating to 50° C. under stirring. The resulting clear homogeneous mixture is cooled at room temperature.
The aqueous solution is slowly added in portions to the oily mixture under stirring. The resulting optically clear microemulsion contains 10 mg/ml of Octreotide acetate.

EXAMPLE 12

Preparation of a w/o Microemulsion Containing Octreotide Acetate a) Preparation of the Aqueous Phase
10 mg of Octreotide acetate are dissolved in 0.1 ml of water for injections added with 2 mg of lysine.
b) Preparation of the Oily Phase
0.59 g of ethyl oleate, 0.25 g of soy lecithin and 0.05 g of caprylic acid are mixed in a suitable vessel, heating to 50° C. under stirring. The resulting clear homogeneous mixture is cooled at room temperature.
The aqueous solution is slowly added in portions to the oily mixture under stirring. The resulting optically clear microemulsion contains 1% of Octreotide acetate.

EXAMPLE 13

Preparation of a w/o Microemulsion Containing Octreotide Acetate 0.59 g of ethyl oleate, 0.25 g of soy lecithin and 0.05 g of caprylic acid are mixed in a suitable vessel, heating to 50° C. under stirring. The resulting clear homogeneous mixture is cooled at room temperature. 0.1 g of water for injections containing 2 mg of lysine, are gradually added under stirring to the oily solution. The resulting optically clear microemulsion is added under stirring with 10 mg of Octreotide acetate. The active ingredient is inbodyrated in said microemulsion within a few seconds. The microemulsion is filtered through a 0.22 mcm polysulfone filter. The resulting optically clear microemulsion, analyzed by HPLC, shows a content in Octreotide acetate of 6.35 mg/ml.

EXAMPLE 14

Preparation of a w/o Microemulsion Containing Myoglobin a) Preparation of the Aqueous Phase
5.5 mg of Myoglobin are dissolved in 1.5 ml of water for injections added with 10 mg of lysine.
b) Preparation of the Oily Phase
2 g of ethyl oleate, 1.2 g of soy lecithin and 0.25 g of caprylic acid are mixed, in a suitable vessel, heating to 50° C. The resulting clear homogeneous mixture is cooled at room temperature.
The aqueous solution is slowly added in portions to the oily mixture under stirring. The resulting optically clear microemulsion contains 1.3 mg/ml of Myoglobin.

EXAMPLE 15

In vivo Evaluation of the Effectiveness of the Microemulsion Containing Leuprolide Acetate Prepared as Described in Examples 1 and 2.

Three groups of Sprague Dawley male rats (10 per each group) were housed for 5 days with water and food ad libitum before treatment.

Two microemulsion formulations prepared as described in Examples 1 and 2, with different concentrations of Leuprolide acetate, namely 3 mg/ml (Example 1) and 6 mg/ml (Example 2) were administered in a single dose, each in a group of rats, at the dose of active corresponding to 0.750 mg/kg.

Control animals (3 per group) received saline solution.

Testosterone plasma levels after taking the blood samples were evaluated at days 1, 2, 3, 4, 7, 14, 21, 28, 42 and 56. Blood samples were centrifuged and serum testosterone was measured by EIA kit.

Serum testosterone levels were evaluated until 60 days after administration.

The results are described in FIG. 1.

The following Table 1 summarizes the data concerning organs weight in the treated animals.

TABLE 1

Effect of the microemulsions prepared as described in Examples 1 and 2 on body and reproductive organs weight in rats.

Body and reproductive organs weight (g) after 28 and 56 days

| Microemulsion | 28 days | | | | 56 days | | | |
|---|---|---|---|---|---|---|---|---|
| | Body | Testes | Prostate | Seminal vesicles | Body | Testes | Prostate | Seminal vesicles |
| Salina | 570.0 ± 13.2 | 3.73 ± 0.09 | 0.72 ± 0.07 | 1.95 ± 0.010 | 631.2 ± 10.1 | 3.54 ± 0.05 | 0.80 ± 0.05 | 1.96 ± 0.26 |
| Example 1 | 546.6 ± 8.8 | 1.84 ± 0.11* | 0.33 ± 0.03* | 0.49 ± 0.08* | 600.0 ± 16.4 | 2.39 ± 0.17* | 0.50 ± 0.03# | 1.39 ± 0.14 |
| Example 2 | 532.8 ± 4.6 | 1.68 ± 0.14* | 0.22 ± 0.03* | 0.25 ± 0.03* | 626.6 ± 25.5 | 2.5 ± 0.2◊ | 0.51 ± 0.08# | 1.43 ± 0.22 |

Data expressed as mean ± standard error of the group (5 animals)
*$p < 0.001$;
◊$p < 0.01$;
$p < 0.05$ vs. saline (ANOVA test and Bonferroni † test for multiple comparisons).

The formulations of the present invention, independently on the concentration of the active in the microemulsion, are free from substantial systemic or local side effects and provide the sustained release of the active ingredient for a duration of at least 30 days and therapeutic efficacy already 48 h after the injection.

The efficacy is comparable to that obtainable when using the commercial depot formulation "Enantone" based on bioerodible polymers.

EXAMPLE 16

Evaluation of the Subcutaneous Tolerability of the Microemulsions

The test for the evaluation of the subcutaneous tolerability was effected by injecting groups of at least 9 rats with a single administration of the microemulsions reported in the following Table 2.

Clinical, post-mortem and histologic examinations were carried out 48 h, 7 days and 14 days after the administration.

TABLE 2

| Compound | Amount (mg) | Presence of swelling (Mean score *) | | | Presence of ulcerations | | |
|---|---|---|---|---|---|---|---|
| | | 48 h | 7 days | 14 days | 48 h | 7 days | 14 days |
| Microemulsion A(1) | 125 μl | 2 | 2 | 1 | No | No | No |

TABLE 2-continued

| Compound | Amount (mg) | Presence of swelling (Mean score *) | | | Presence of ulcerations | | |
|---|---|---|---|---|---|---|---|
| | | 48 h | 7 days | 14 days | 48 h | 7 days | 14 days |
| Microemulsion A(1) | 500 μl | 3 | 3 | 2.5 | No | No | No |
| Microemulsion B(2) | 125 μl | 3 | 3 | 3 | Yes | Yes | Yes |

(1)Microemulsion prepared as described in Example 1.
(2)Microemulsion prepared as described in Example 8.
* disclosure of the score: 1 slight effect; 2 moderate; 3 severe.

This test considers biologically compatible the formulations which induce no persistent local ulcerations, whereas the presence of swelling is a function of the amount of product injected and of the rate of elimination of the ethyl oleate from subcutaneous tissues, as described by Howard et al. in Int. J. Pharm. 16 (1983) 31–39.

EXAMPLE 17

In vivo Evaluation of the Effectiveness of the Microemulsion Containing Octreotide Acetate A dose corresponding to 6 mg/rat of microemulsion containing Octreotide prepared as described in Example 11 was administered to 6 male rats weighing about 175–200 g. Plasma samples were taken before the administration of the compound and 0.5 hours, 24 hours, 4, 6 and 8 days after treatment.

Octreotide was extracted from plasma and analyzed with LC-MS-MS apparatus vs. a calibration curve. Plasma levels are reported in the following table 3:

TABLE 3

| Time of sampling | 0.5 h | 24 h | 4 days | 6 days | 8 days |
|---|---|---|---|---|---|
| Octreotide (ng/ml) | 539 | 40.2 | 62.5 | 4.5 | 7.6 |

Significant Octreotide plasma levels were found until 8 days after treatment.

EXAMPLE 18

Evaluation of the Dose/Efficacy Ratio of the Microemulsion Containing Leuprolide Acetate The formulation containing Leuprolide acetate, prepared as described in Example 2, was administered to rats, in a single dose of 2.25 mg/kg (Example). Control animals received a corresponding dose of saline solution (Control).

Testosterone plasma levels on blood samples were evaluated at days 0, 1, 2, 3, 5, 7, 14, 21, 28, 42 and 56. Blood samples were centrifuged and serum testosterone was measured by an Elisa kit.

Figure 2:
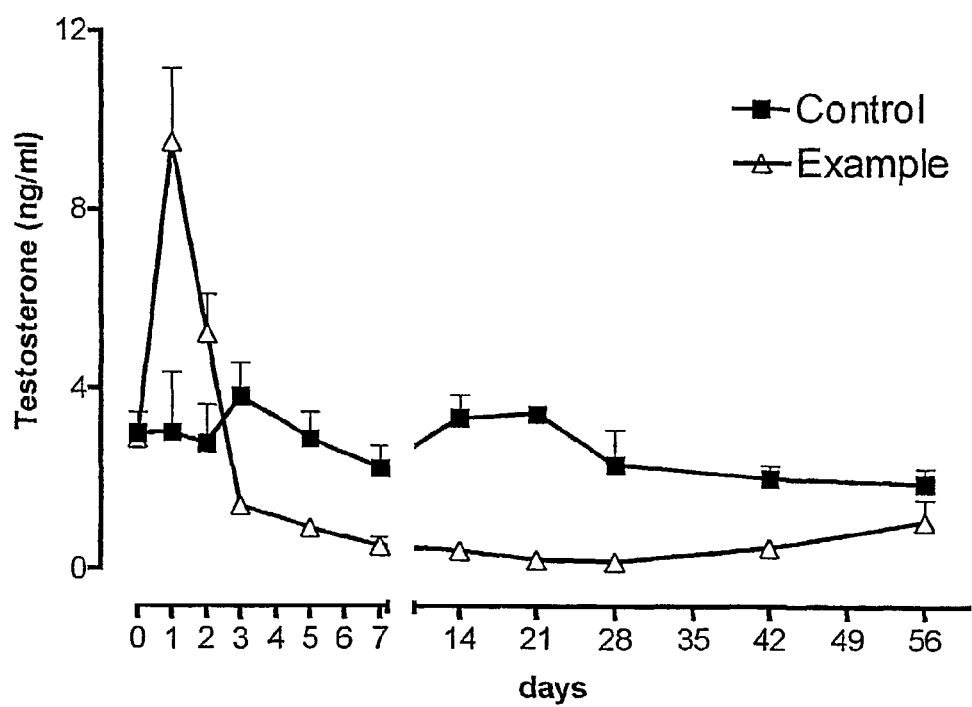

Results are shown in FIG. 2.

The data concerning organs weights in treated animals are summarized in the following Table 4.

Table 4: Effect of a Leuprolide acetate microemulsion or of a saline solution on the body and reproductive organs weight in rats (Example and Control).

| | Body and reproductive organs weight (g) on 56 day | | | |
|---|---|---|---|---|
| | Body | Testes | Prostate | Seminal vesicles |
| Control | 645 ± 34 | 3.73 ± 0.16 | 0.82 ± 0.04 | 1.96 ± 0.09 |
| Example | 608 ± 35 | 1.94 ± 0.42 | 0.35 ± 0.14 | 0.55 ± 0.16 |
| | | ($p < 0.01$) | ($p < 0.5$) | ($p < 0.05$) |

Reduction of both testosterone plasma levels and reproductive organs weight is clearly evidenced 56 days after the administration of the microemulsion.

The invention claimed is:

1. A water-in-oil (w/o) microemulsion comprising:
   a) up to 20% of an internal hydrophilic aqueous phase containing a therapeutically active hydrophilic compound;
   b) 30 to 98% of a hydrophobic external phase selected from esters of $C_8$–$C_{20}$ saturated or unsaturated carboxylic acids with a $C_2$–$C_8$ branched or linear alcohol residue or mono, di- and triglycerides of $C_8$–$C_{20}$ fatty acids;
   c) up to 50% of a surfactant in admixture with a co-surfactant, said surfactant being selected from natural or synthetic glycerophospholipids containing residues of $C_4$–$C_{20}$ saturated or unsaturated carboxylic acids having as phosphoester moiety a residue of choline, ethanolamine, serine, glycerol, and said co-surfactant being selected from $C_8$–$C_{20}$ fatty acids or $C_2$–$C_{12}$ alcohols, and wherein the surfactant/co-surfactant ratio is $\geq 2$;
   wherein the aqueous phase has a pH between 4.5 and 7.5.

2. The microemulsion of claim 1,
   which induces no local ulcerogenicity, but which may produce non-persistent granulomas.

3. The microemulsion of claim 1, wherein the therapeutically active compound comprises a peptide, protein, oligosaccharide or polysaccharide.

4. The microemulsion of claim 1, wherein the therapeutically active compound is a peptide.

5. The microemulsion of claim 1, wherein the therapeutically active compound is an LHRH hormone peptide analog.

6. The microemulsion of claim 1, wherein the therapeutically active compound is Leuprolide acetate, Goserelin, Triptorelin, Nafarelin, Histrelin, Cetrorelix or the corresponding acetates.

7. The microemulsion of claim 1, which provides sustained release of the therapeutically active compound for at least 30 days.

8. The microemulsion of claim 1, wherein the therapeutically active compound is Somatostatin, Octreotide or Lanreotide.

9. The microemulsion of claim 1, which provides sustained release of the therapeutically active compound for at least 8 days.

10. The microemulsion of claim 1, wherein the therapeutically active compound is an oligosaccharide or a polysaccharide.

11. The microemulsion of claim 1, wherein the therapeutically active compound is unfractioned heparin or one or more low molecular weight heparins.

12. The microemulsion of claim 1, wherein the therapeutically active compound has been made hydrophilic by being derivatized.

13. The microemulsion of claim 1, wherein the surfactant is selected from the group consisting of:
   a) natural or synthetic glycerophospholipids containing residues of at least one $C_4$–$C_{20}$ saturated or unsaturated carboxylic acids, having as phosphoester moiety a residue of choline, ethanolamine, serine, or glycerol;
   b) cholesterol;
   c) sugars of $C_{12}$–$C_{20}$ fatty acid esters; and
   d) polyoxyethylene sorbitan $C_{12}$–$C_{20}$ fatty acid esters.

14. The microemulsion of claim 1, wherein the co-surfactant is selected from the group consisting of $C_8$–$C_{20}$ fatty acids; $C_2$–$C_{14}$ polyhydroxyalkanes; $C_2$–$C_{12}$ alcohols; and esters of lactic acid with a $C_2$–$C_8$ alcohol residue.

15. The microemulsion of claim 1 wherein the hydrophobic continuous phase comprises one or more of the following compounds: an ester of a $C_8$–$C_{20}$ saturated or unsaturated carboxylic acid with a $C_2$–$C_8$ alcohol residue, a mono, di- or triglyceride of a $C_8$–$C_{20}$ fatty acid, or a vegetable oil.

16. The microemulsion of claim 1, wherein the aqueous phase has a pH between 5 and 7.

17. The microemulsion of claim 1, further comprising one or more natural amino acids to adjust the pH to 4.5 to 7.5.

18. A method for preparing a medicament comprising:
   admixing the microemulsion of claim 1 with Leuprolide, Goserelin, Triptorelin, Nafarelin acetate, Histrelin, Cetrorelix or the corresponding acetates or other LHRH analogs, and formulating said medicament to suppress testosterone production after single administration for at least 30 days, and to decrease the testosterone level 48 h after the administration.

19. A method for preparing a medicament comprising:
   admixing the microemulsion of claim 1 with Octreotide or its analogues,
   and formulating said medicament to suppress growth hormone production for at least 8 days.

20. A method for preparing a medicament comprising:
   admixing the microemulsion of claim 1 with unfractioned heparin or one or more low molecular weight heparins, wherein said medicament is formulated for sustained release after a single administration.

21. A water-in-oil (w/o) microemulsion consisting of:
   a) up to 20% of an internal hydrophilic aqueous phase containing a therapeutically active hydrophilic compound which has a pH between 4.5 and 7.5;

b) 30 to 98% of a hydrophobic external phase selected from esters of $C_8$–$C_{20}$ saturated or unsaturated carboxylic acids with a $C_2$–$C_8$ branched or linear alcohol residue or mono, di- and triglycerides of $C_8$–$C_{20}$ fatty acids;

c) up to 50% of a surfactant in admixture with a co-surfactant, said surfactant being selected from natural or synthetic glycerophospholipids containing residues of $C_4$–$C_{20}$ saturated or unsaturated carboxylic acids having as phosphoester moiety a residue of choline, ethanolamine, serine, glycerol, and said co-surfactant being selected from $C_8$–$C_{20}$ fatty acids or $C_2$–$C_{12}$ alcohols, and wherein the surfactant/co-surfactant ratio is $\geqq 2$.

22. The water-in-oil (w/o) microemulsion of claim 21, which contains $\leqq 35\%$ of a surfactant/cosurfactant mixture having a ratio of surfactant to cosurfactant of $\geqq 3.5$.

* * * * *